United States Patent

Günther et al.

[11] Patent Number: 4,915,868
[45] Date of Patent: Apr. 10, 1990

[54] OPTICALLY ACTIVE ESTERS OF 1-ACYLPROLINE AS DOPES IN LIQUID-CRYSTAL MIXTURES, AND NOVEL OPTICALLY ACTIVE ESTERS OF 1-ACYLPROLINE

[75] Inventors: Dieter Günther, Kelkheim; Dieter Ohlendorf, Liederbach; Rainer Wingen, Hattersheim am Main, all of Fed. Rep. of Germany

[73] Assignee: Hoechst Aktiengesellschaft, Frankfurt am Main, Fed. Rep. of Germany

[21] Appl. No.: 136,595

[22] Filed: Dec. 22, 1987

[30] Foreign Application Priority Data

Dec. 24, 1986 [DE] Fed. Rep. of Germany ....... 3644522

[51] Int. Cl.⁴ .................. C09K 19/52; C09K 19/34; G02F 1/13
[52] U.S. Cl. .................. 252/299.61; 252/299.01; 350/350 R; 350/350 S; 548/533; 544/316; 544/318; 544/298; 544/335
[58] Field of Search .............. 252/299.01, 299.61; 350/350 R, 350 S; 548/533; 544/238, 335, 298, 316, 318, 372

[56] References Cited

U.S. PATENT DOCUMENTS 4,349,452 9/1982 Osman et al. .................. 252/299.61
4,764,619 8/1988 Gunjima et al. ................ 252/299.61

FOREIGN PATENT DOCUMENTS

86/02937 5/1986 PCT Int'l Appl. .

Primary Examiner—John F. Terapane
Assistant Examiner—J. E. Thomas
Attorney, Agent, or Firm—Curtis, Morris & Safford

[57] ABSTRACT

Optically active esters of 1-acylproline of the general formula

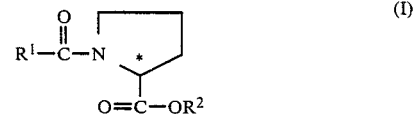

in which at least one of the radicals $R^1$ and $R^2$ is a mesogenic radical, are suitable as dopes in ferroelectric liquid-crystal mixtures. Proline derivatives in which only the $R^1$ radical is mesogenic are preferred.

4 Claims, No Drawings

OPTICALLY ACTIVE ESTERS OF 1-ACYLPROLINE AS DOPES IN LIQUID-CRYSTAL MIXTURES, AND NOVEL OPTICALLY ACTIVE ESTERS OF 1-ACYLPROLINE

Especially in the last decadge, liquid crystals have been introduced into a very wide variety of industrial areas in which electrooptical and display device properties are in demand (e.g. in displays for watches, pocket calculators and typewriters). These display devices are based on dielectric alignment effects in nematic, cholesteric and/or smectic phases or liquid-crystalline compounds, where—caused by the dielectric anisotropy—the longitudinal molecular axis of the compounds adopts a preferred alignment in an applied electrical field. The usual switching times in these display devices are rather too slow for many other potential areas of application of liquid crystals, which are per se very promising chemical compounds for industry due to their unique properties. This disdavantage is particularly noticeable when—which is necessarily the case in relatively large display element areas—it is necessary to address a large number of image points, which means that the production costs of such equipment containing these relatively large areas, such as video equipment, oscillographs or TV, radar, EDP or word processor screens, would be too high.

Besides the nematic and cholesteric liquid crystals, tilted smectic liquid-crystal phases have for a few years also become increasingly important for practical applications. If suitable dopes which exhibit or induce in the liquid-crystal phase so-called spontaneous polarization ($P_s$) are added to such tilted smectic phases, in particular smectic C ($S_c$) phases, the phases can be converted into a ferroelectric liquid-crystal phase (denomination of $P_s$ in $nC.cm^{-2}$).

Clark and Lagerwall have been able to show that the use of such liquid-crystal systems in very thin cells leads to optoelectric display elements which, compared to conventional TN ("twisted nematic") cells, have switching times which are faster by a factor of about 1000 (cf., for example, Lagerwall et al. "Ferroelectric Liquid Crystals for Displays", SID Symposium, October Meeting 1985, San Diego, Ca., USA). As a consequence of these and other favorable properties, for example the possibility for bistable switching and the control which is virtually independent of the view angle, FLCs are, in principle, highly suitable for the abovementioned areas of application, for example via matrix addressing.

For practical use of ferroelectric liquid crystals in optoelectric displays, chirally smectic phases, for example $S_c$ phases, are required which are stable over a large temperature range and have high spontaneous polarization ($P_s$) and short switching times ($\tau$). It has been attempted to achieve this goal using liquid-crystalline compounds or mixtures of liquid-crystalline compounds which themselves have, for example, a $S_c$ phase and exhibit ferroelectric behavior (D. M. Walba, U.S. Pat. No. 4,556,727). However, this is subject to limits. Greater opportunities are presented when liquid-crystalline compounds or mixtures of such compounds which have a smectic phase, but are not themselves optically active, are doped with an optically active compound, which need not itself be liquid crystalline.

There is therefore a demand for compounds which induce high spontaneous polarization and lead to short switching times when added in small amounts to non-optically active liquid-crystalline compounds or mixtures.

It has now been found that optically active esters of 1-acylproline as dopes in such mixtures lead to very short switching times even in low amounts.

The invention therefore relates to the use of optically active esters of 1-acylproline as dopes in liquid-crystal systems which contain optically active esters of 1-acylproline and to novel optically active esters of 1-acylproline.

WO 86/02937 discloses that chiral derivatives of natural amino acids are suitable as dopes for producing $S_c$ phases. However, the amino nitrogen is not part of a ring system in the compounds described therein.

The esters of 1-acylproline to be used according to the invention as dopes in liquid-crystal mixtures correspond to the general formula (I)

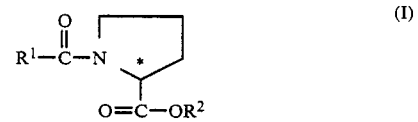

At least one of the radicals $R^1$ and $R^2$ is preferably a mesogenic radical, and it is preferred that only the $R^1$ radical is mesogenic.

In particular, $R^1$ or $R^2$ is a radical of the formula (II)

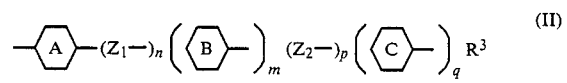

where the indices and components have the following meaning:

n, m, p and q=zero or 1, but p=zero when m=zero, $Z_1$=COO, OOC, $(CH_2)_2$, $OCH_2$, $CH_2O$,

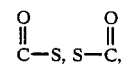

$Z_2=Z_1$ or $CH_2$, N=N, N=N(O),

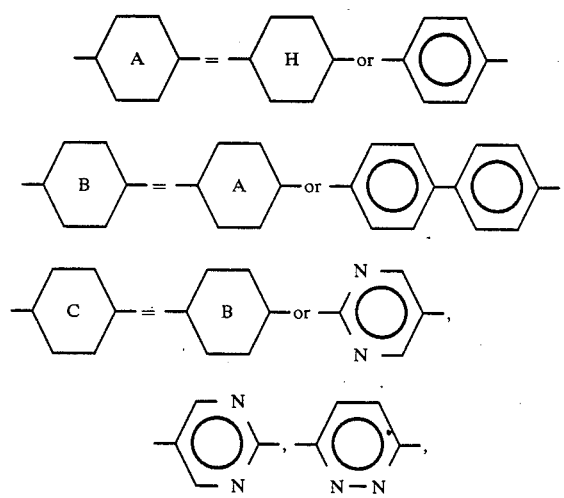

-continued

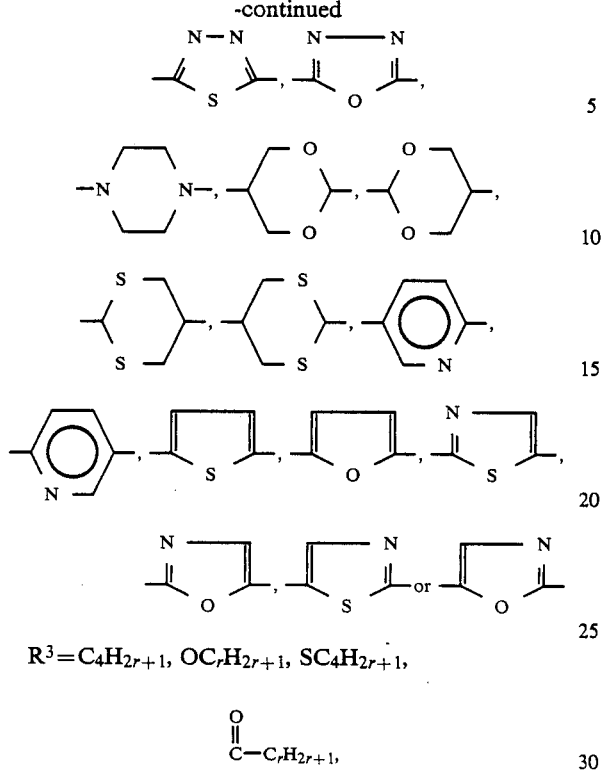

$R^3 = C_4H_{2r+1}$, $OC_rH_{2r+1}$, $SC_4H_{2r+1}$,

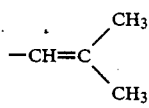

$OOC-C_4H_{2r+1}$, $COOC_rH_{2r+1}$ or $NHC_rH_{2r+1}$, where r is an integer from 1-20 when m, p and q=zero and n=zero or 1, and an integer from 1 to 12 when n=zero or 1 and at least one of the indices m, p and q is 1, and in which the other radical $R^1$ or $R^2$ is: a straight-chain or branched alkyl group which has 1-12 carbon atoms, which is unsubstituted or substituted by F, Cl, Br or CN, in which one or two non-neighboring —CH$_2$- groups may be replaced by —O—, —S—, —CO—, —OCO—, —COO—, —OCS—, —COS— and/or —CH=CH—, and which can contain a terminal group —CH=CH$_2$ or

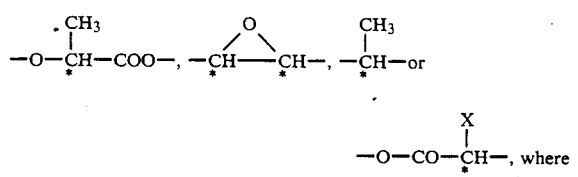

or which is cyclohexyl or phenyl, or 4-alkylcyclohexyl or 4-alkylphenyl having 1-6 carbon atoms in the alkyl group, or which is an optically active group having a chiral component from the group comprising $$-O-\underset{*}{CH}-COO-,\ -\underset{*}{CH}\overset{O}{-}\underset{*}{CH}-,\ -\underset{*}{CH}-\ \text{or}$$

$$-O-CO-\underset{*}{CH}-,\ \text{where}$$

$X=F$, Cl, Br or CN.

In an embodiment of the invention, at least one of the radicals $R^1$ and $R^2$ in formula (I) is a mesogenic radical.

In particular at least one of the radicals $R^1$ and $R^2$ in formula (I) is a mesogenic radical from the group comprising

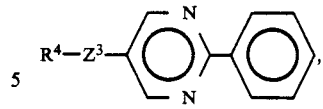

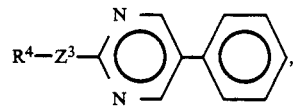

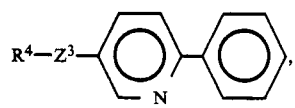

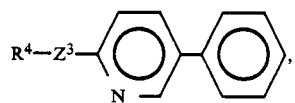

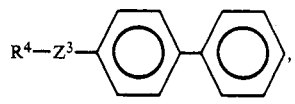

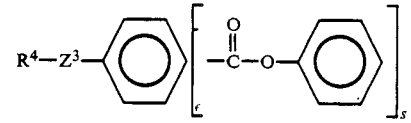

where s=1 or 2,
$Z_3$ is a chemical bond, an oxygen atom, a sulfur atom or a carboxyl group, and $R^4$ is a straight-chain or branched, saturated or unsaturated alkyl group having 6-12 carbon atoms.

In this embodiment, the nonmesogenic radical is: a cycloalkyl group, in particular a cyclohexyl group, or a phenyl, alkylphenyl or alkoxyphenyl group, or a straight-chain or branched alkyl group having 1-10 carbon atoms or an unsaturarted alkyl group having 2-10 carbon atoms, or an alkyl group in which one —CH$_2$—group is replaced by

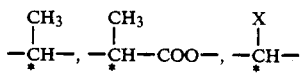

where X=F, Cl, Br or CN, or by

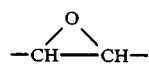

Examples of an ester of 1-acylproline according to the present invention are
methyl ester of 1-(4-palmityloxy)-benzoyl-(S)-(—)-proline
[4-(5-octylpyrimidin-2-yl)-phenyl]ester of 1-hexanoyl-(S)-(—)-proline
n-butyl ester of 1-[4-(4-octyloxybenzoyl)-oxybenzoyl]-(S)-(—)-proline
methyl ester of 1-(4-decyloxybenzoyl)-(S)-(—)-proline
ethyl ester of 1-(4-decyloxybenzoyl)-(S)-(—)-proline
n-hexyl ester of 1-(4-decyloxybenzoyl)-(S)-(—)-proline
n-octyl ester of 1-(4-decyloxybenzoyl)-(S)-(—)-proline methyl ester 1-(4-stearyloxybenzoyl)-(S)-(−)-proline
methyl ester of 1-[4-(4-octyloxybenzoyl)-oxybenzoyl]-(S)-(−)-proline
n-hexyl ester of 1-[4-(4-octyloxybenzoyl)-oxybenzoyl]-(S)-(−)-proline
cyclohexyl ester of 1-[4-(4-octyloxybenzoyl)-oxybenzoyl]-(S)-(−)-proline
n-octyl ester of 1-[4-(4-octyloxybenzoyl)-oxybenzoyl]-(S)-(−)-proline
[4-(5-octylpyrimidin-2-yl)-phenyl]ester of 1-acetyl-(S)-(−)-proline
[4-(5-octylpyrimidin-2-yl)-phenyl]ester of 1-propionyl-(S)-(−)-proline
[4-(5-octylpyrimidin-2-yl)-phenyl]ester of 1-butyryl-(S)-(−)-proline
[4-(5-octylpyrimidin-2-yl)-phenyl]ester of 1-octanoyl-(S)-(−)-proline
[4-(5-octylpyrimidin-2-yl)-phenyl]ester of 1-decanoyl-(S)-(−)-proline
[4-(5-octylpyrimidin-2-yl)-phenyl)ester of 1-cyclohexyloyl-(S)-(−)-proline
[4-(5-octylpyrimidin-2-yl)-phenyl]ester of 1-benzoyl-(S)-(−)-proline
[4-(5-octylpyrimidin-2-yl)-phenyl]ester of 1-(4-palmityloxy)-benzoyl-(S)-(−)-proline
[4-(5-octylpyrimidin-2-yl)-phenyl]ester of 1-[4-(4-octyloxybenzoyl)-oxybenzoyl]-(S)-(−)-proline
[4-(4-decyloxybenzoyl)-oxyphenyl]ester of 1-[4-(4-octyloxybenzoly)-oxybenzoyl]-(S)-(−)-proline
[4-(4-decyloxybenzoyl)-oxyphenyl]ester of 1-propionyl-(S)-(−)-proline
[4-(4-decyloxybenzoyl)-oxyphenyl]ester of 1-hexanoyl-(S)-(−)-proline
[4-(4′-octyloxy)-diphenyl]ester of 1-hexanoyl-(S)-(−)-proline
[4-(2-octylpyrimidin-5-yl)-phenyl]ester of 1-hexanoyl-(S)-(−)-proline
[4-(5-octylpyrimidin-2-yl)-phenyl]ester of 1-(2-chloro-4-methylpentanoyl)-(S)-(−)-proline
isobutyl ester of 1-[4-(4-octyloxybenzoyl)-oxybenzoyl]-(S)-(−)-proline
[4-(1-ethoxycarbonyl)-1-ethoxy]phenyl ester of 1-(4-decyloxybenzoyl)-(S)-(−)-proline
[4-(2-octyloxypyrimidin-5-yl)-phenyl]ester of 1-(4-decyloxybenzoyl)-(S)-(−)-proline
[4-(2-octylthiopyrimidin-5-yl)-phenyl]ester of 1-(4-decyloxybenzoyl)-(S)-(−)-proline
[4-(2-octyloxypyrimidin-5-yl)-phenyl]ester of 1-hexanoyl-(S)-(−)-proline
[4-(2-octylthipyrimidin-5-yl)-phenyl]ester of 1-hexanoyl-(S)-(−)-proline
[4-(S-octylpyrimidin-2-yl)-phenyl]ester of 1-[2S,3S)-2-chloro-3-methylpentanoyl]-(S)-proline
[(R)-2-butyl]ester of 1-[4-(4-decyloxybenzoyloxy)-benzoyl]-(S)-proline
[(S)-1-ethoxycarbonylethyl]ester of 1-[4-(4-octyloxybenzoyloxy)benzoyl]-(S)-proline
[(S)-2-chloropropyl]ester 1-[4-(4-octyloxybenzoyloxy)-benzoyl]-(S)-proline
methyl ester of 1-(4′-octylbiphenyl-4-yl)carbonyl-(S)-proline
octyl ester of 1-(4′-octylbiphenyl-4-yl)carbonyl-(S)-proline
octyl ester of 1-(4′-octyloxybiphenyl-4-yl)carbonyl-(S)-proline
octyl ester of 1-[4-(5-octylpyrimidin-2-yl)benzoyl]-(S)-proline In another embodiment, the present invention is directed to a display element containing a liquid-crystal mixture containing at least one optically active ester of 1-acylproline.

The phenol or benzoic acid derivatives employed for introducing mesogenic radicals are compounds which are known from the literature.

In order to prepare the compounds of the formula (I), proline, protected at the nitrogen, is esterified in a manner which is known per se using the appropriate phenol or alcohol, namely in the presence of Bronstedt or Lewis acids, if appropriate in the presence of water-binding agents or with the aid of condensing agents, such as N,N′-carbonyldiimidazole or dicyclohexylcarbodiimide.

The N-acylation takes place, after removal of the protecting group, using the appropriate carboxylic acids or carbonyl chlorides in the presence of dicyclohexylcarbodiimide or in the presence of organic bases such as pyridine or triethylamine.

The liquid-crystal mixtures according to the invention form liquid-crystal phases and contain at least one optically active compound of the general formula (I).

The term "liquid-crystal phase" is taken to mean neamtic, cholesteric, smectic or tilted smectic phases, in particular $S_c$ phases. The liquid-crystal mixtures comprise 2 to 20, preferably 2 to 15, components, including at least one of the chiral compounds claimed according to the invention.

The other components are preferably selected from know compounds having nematic, cholesteric and/or smectic phases, for example $S_A$ phases, and/or tilted smectic phases; these include, for example, Schiff bases, biphenyls, ter-phenyls, phenylcyclohexanes, cyclohexylbiphenyls, N-, S- or O-containing heterocyclic compounds, for example pyrimidines, cinnamates, cholesterol esters and various bridged, multinuclear p-alkylbenzoates with polar terminal groups. In general, the commercially available liquid-crystal mixtures are already present, before addition of the optically active compound(s), as mixtures of a very wide variety of components, of which at least one is mesogenic, i.e. as the compound, in derivatized form or mixed with certain cocomponents, exhibits a liquid-crystal phase which gives expectations of at least one enantiotropic (clear point > melting point) or montropic (clear point < melting point) mesophase formation. In addition to at least one of the optically active compounds claimed according to the invention, the liquid-crystal mixture contains, in particular, one ester compound having an $S_c$ phase, for example a phenyl alkoxybenzoate, or a biaromatic compound having a nitrogen-containing heterocyclic ring, for example an alkylpyrimidinylalkoxybenzene. The liquid-crystal mixtures generally contain 0.05 to 70% by weight, in particular 0.1 to 50% by weight, of the compound(s) according to the invention.

The compounds according to the invention are suitable, in particular, as dopes for tilted smectic liquid-crystal phases since they convert the latter into ferroelectric liquid-crystal phases; the values for spontaneous polarization ($P_s$) on 10 mol % doping are in the range from about 4–40 nCb/cm$^2$ and in the range from about 40–400 nCb/cm$^2$ extrapolated to the pure compound.

The switching times for the novel systems are usually significantly below 100 μs.

PREPARATION EXAMPLES

Example 1

Methyl ester of 1-(4-palmityloxy)-benzoyl-(S)(—)proline 10.9 g (30 mmol) of 4-palmityloxybenzoic acid are refluxed for 1 hour with 50 ml of thionyl chloride. The excess thionyl chloride is then distilled in vacuo. A crystalline residue remains which is introduced into a solution of 5 g of S-proline methyl ester chlorohydrate in 50 ml of pyridine at room temperature. The mixture is stirred at room temperature for 4 hours, poured into 400 ml of ice water and adjusted to pH 3–4 using concentrated hydrochloric acid. The precipitated product is filtered off under suction, washed with water and dried at 40° C. in vacuo. The crude product is then recrystallized from methanol. 13.15 g (92% of theory) of the desired compound are obtained as colorless crystals of melting point 69°–70° C. $[\alpha]_D^{20}$: −33.6° (C=1, CH$_2$Cl$_2$).

Example 2

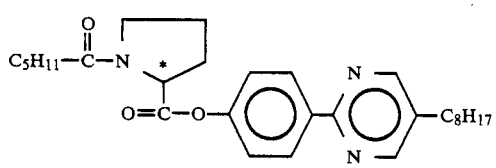

A. 12.5 g (50 mmol) of N-carbobenzoxy-S-proline are dissolved in 100 ml of methylene chloride together with 14.2 g (50 mmol) of 2-(4-hydroxyphenyl)-5-n-octylpyrimidine and 0.75 g (5 mmol) of 5-pyrrolidinopyridine, and the mixture is cooled to 0° C. 11.1 g (54 mmol) of dicyclohexylcarbodiimide are then added. The mixture is stirred at 0°–5° C. for 2 hours, dicyclohexylurea precipitating. The temperature is then allowed to increase to room temperature, and the mixture is stirred for a further 5 hours. Dicyclohexylurea is filtered off under suction (11.35 g, 94% of theory), and the solvent is stripped off. The crude product which crystallizes during this procedure is recrystallized from 50 ml of methanol. 18.7 g (72% of theory) of the compound

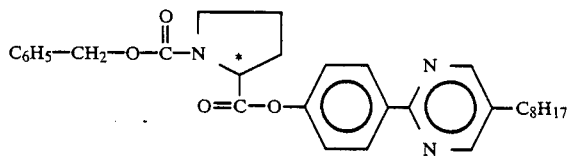

are obtained. Melting point: 97°–98° C. $[\alpha]_D^{22}$: −68.5° (C=1, CH$_2$Cl$_2$).

B. 5.2 g (10 mmol) of the compound formed under A are slurried in 6 ml of glacial acetic acid, and 6 ml of HBr/glacial acetic acid (30% strength) are added while stirring. The evolution of carbon dioxide is complete after 30 minutes. The mixture is diluted with 80 ml of dry diethyl ether, the hydrobromide of the ester of S-proline precipitating as an oil. After 2 hours, the diethyl ether is decanted off, and the residue is again stirred for 3 hours with a further 70 ml of diethyl ether, the hydrobromide solidifying. The product is rapidly filtered off under suction, washed with diethyl ether and dried in vacuo, and is further reacted without further purification.

C. 1.38 ml of n-hexyanoyl chloride are added to 4.6 g (10 mmol) of the hydrobromide prepared under B in 25 ml of methylene chloride, and the mixture is cooled to 0° C. 3.1 ml of triethylamine in 8 ml of methylene chloride are then added dropwise over the course of 5 minutes. The mixture is then stirred for a further 15 minutes at 0°–5° C. and 1 hour at room temperature. The solvent is removed by distillation in vacuo, and the residue remaining is recrystallized from n-hexane. 1.2 g (25% of theory) of the title compound are obtained. Melting point: 46°–47° C. $[\alpha]_D^{22}$: −54° (C=1, CH$_2$Cl$_2$)

Example 3

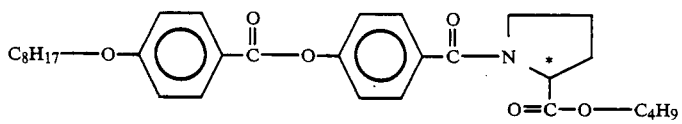

A. 5 g (20 mmol) of N-carbobenzoxy-S-proline are dissolved in 40 ml of methylene chloride with 1.9 ml (20.8 mmol) of n-butanol and 0.3 g (2 mmol) of 4-pyrrolidinopyridine, and the mixture is cooled to 0° C. while stirring. 4.5 g (22 mmol) of dicyclohexylcarbodiimide are then added, and the temperature is held at 0° C. to 5° C. for a further 2 hours.

The mixture is allowed to stand at room temperature for a further 24 hours, and the precipitated dicyclohexylurea is filtered off under suction. The mother liquor is evaporated in vacuo, 50 ml of diisopropyl ether are added to the residue, urea is again filtered off, and the mother liquor is again evaporated. An oily residue remains which is chromatographed over 400 g of silica gel using methylene chloride/3% by volume of methanol. 4.1 g (67% of theory) of the n-butyl ester of N-carbobenzoxy-S-proline are obtained as an oil. $[\alpha]_D^{20}$: −47.7° (C=1, CH$_2$Cl$_2$)

B. 7 ml of glacial acetic acid and 6 ml of HBr/glacial acetic acid (33% strength) are added at room temperature to 3.75 g (12.3 mmol) of the ester of Z-S-proline formed under A, and the mixture is stirred until the evolution of carbon dioxide is complete (about 60 minutes). 70 ml of diethyl ether are added. The mixture is separated from the oil which deposits, and the latter is dried at room temperature in a high vacuum. 2.9 g (93% of theory) of a yellowish oil are obtained which can be further reacted without further purification.

C. 4.55 g (12.3 mmol) of 4-(4-octyloxybenzoyloxy)-benzoic acid are stirred for 1 hour under reflux with 20 ml of thionyl chloride. The solution is then freed from excess thionyl chloride in vacuo (crystallization). The residue is dissolved in 15 ml of methylene chloride and added to a solution, cooled to 0° C., of 2.9 g of the hydrobromide prepared under B in 15 ml of methylene chloride. 3.8 ml (27 mmol) of triethylamine in 8 ml of methylene chloride are then added dropwise over the course of 10 minutes at 0° to 5° C.

The mixture is stirred for a further 15 minutes at 0° C. and for 1 hour at room temperature and filtered, and the mother liquor is evaporated to dryness in vacuo. A semicrystalline residue is obtained which is chromatographed over 220 g of silica gel using methylene chloride/10% by volume of methanol as eluant. 4.5 g of an oil remain which, according to thin-layer chromatography and H-NMR, is not yet pure. It is therefore re-chromatographed over 200 g of silica gel using n-hexane/20% by volume n-butanol. 3.6 g (56% of theory, relative to the carboxylic acid employed, of the title compound are obtained as a colorless oil. $[\alpha]_D^{21}$: $-31.1°$ (C=1, $CH_2Cl_2$). The compound exhibits the following phase behavior: crystalline $-15°$ C. cholesteric 14.5° C. isotropic.

Table I

TABLE I

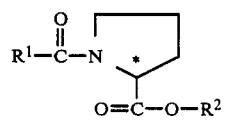

| Example No. | $R^1$ | $R^2$ | C [°C.]I | Rotation [degree] (C = 1, $CH_2Cl_2$) |
|---|---|---|---|---|
| 1 | $C_{16}H_{33}-O-\langle\bigcirc\rangle-$ | $CH_3$ | 69–70 | $[\alpha]_D^{22}$: $-33.6°$ |
| 2 | $C_5H_{11}$ | $\langle\bigcirc\rangle-\langle N{=}{=}N\rangle-C_8H_{17}$ | 97–98 | $[\alpha]_D^{22}$: $-68.5°$ |
| 3 | $C_8H_{17}O-\langle\bigcirc\rangle-$ | $n\text{-}C_4H_9$ | oil | $[\alpha]_D^{22}$: $-31.1°$ |
| 4 | $C_{10}H_{21}-O-\langle\bigcirc\rangle-$ | $CH_3$ | 49–50 | $[\alpha]_D^{22}$: $-40.7°$ |
| 5 | " | $C_2H_5$ | oil isotropic to $-20°$ | $[\alpha]_D^{21}$: $-30.7°$ |
| 6 | " | $C_4H_9$ | oil isotropic to $-20°$ | $[\alpha]_D^{20}$: $-28.8°$ |
| 7 | " | $C_6H_{13}$ | oil isotropic to $-20°$ | $[\alpha]_D^{21}$: $-26.6°$ |
| 8 | " | $C_8H_{17}$ | oil | $[\alpha]_D^{22}$: $-21.6°$ |
| 9 | $C_{16}H_{33}-O-\langle\bigcirc\rangle-$ | $C_6H_{13}$ | oil | $[\alpha]_D^{22}$: $-21.3°$ |
| 10 | $C_{18}H_{37}O-\langle\bigcirc\rangle-$ | $CH_3$ | 63–66 | $[\alpha]_D^{20}$: $-25.5°$ |
| 11 | $C_8H_{17}O-\langle\bigcirc\rangle-C(=O)-O-\langle\bigcirc\rangle-$ | $CH_3$ | 60.9 [9.2 Ch 28] [9.2 Ch 28] | $[\alpha]_D^{20}$: $-38.3°$ |
| 12 | " | $C_2H_5$ | oil | 3955 $[\alpha]_D^{21}$: $-29.5°$ |
| 13 | " | $C_6H_{13}$ | oil $-11$ Ch 9.6 | $[\alpha]_D^{21}$: $-29.4°$ |

TABLE I-continued $$R^1-\overset{\overset{O}{\|}}{C}-N\underset{O=C-O-R^2}{\overset{*}{\diagdown}}$$

| Example No. | $R^1$ | $R^2$ | C [°C.]I | Rotation [degree] (C = 1, CH$_2$Cl$_2$) |
|---|---|---|---|---|
| 14 | " | ⬡—H | oil | $[\alpha]_D^{21}$: −29.2° |
| 15 | " | C$_8$H$_{17}$ | −2.5 Ch 15.1 | $[\alpha]_D^{21}$: −28.3° |
| 16 | CH$_3$ | ⬡—(pyrimidine)—C$_8$H$_{17}$ | 48 | $[\alpha]_D^{22}$: −58.4° |
| 17 | C$_2$H$_5$ | " | 63–64 | $[\alpha]_D^{22}$: −63.3° |
| 18 | C$_3$H$_7$ | " | 51–53 | $[\alpha]_D^{20}$: −56.5° |
| 19 | C$_7$H$_{15}$ | " | 68–69 | $[\alpha]_D^{22}$: −51.3° |
| 20 | C$_9$H$_{19}$ | ⬡—(pyrimidine)—C$_8$H$_{17}$ | 77–78 | $[\alpha]_D^{22}$: −49.7° |
| 21 | ⬡—H | " | 106–07 | $[\alpha]_D^{22}$: −50.6° |
| 22 | ⬡ | " | 77–78 | $[\alpha]_D^{21}$: −50.4° |
| 23 | C$_{16}$H$_{33}$—O—⬡ | " | 91–93 | $[\alpha]_D^{20}$: −42.8° |
| 24 | C$_8$H$_{17}$O—⬡—C(O)O—⬡ | " | 114 | $[\alpha]_D^{21}$: −28.4° |
| 25 | " | ⬡—O—C(O)—⬡—O—C$_{10}$H$_{21}$ | 122–23 | $[\alpha]_D^{21}$: −24.2° |
| 26 | C$_2$H$_5$ | " | 61–62 | $[\alpha]_D^{22}$: −48.1° |
| 27 | C$_5$H$_{11}$ | " | 51–52 | $[\alpha]_D^{22}$: −44.0° |
| 28 | " | ⬡—⬡—O—C$_8$H$_{17}$ | 83–85 | $[\alpha]_D^{20}$: −53° |
| 29 | " | ⬡—(pyrimidine)—C$_8$H$_{17}$ | 57–58 | $[\alpha]_D^{20}$: −55.5° |

TABLE I-continued $$R^1-\overset{O}{\underset{\|}{C}}-N\overset{*}{\underset{O=C-O-R^2}{\diagdown}}$$

| Example No. | R¹ | R² | C [°C.]I | Rotation [degree] (C = 1, CH₂Cl₂) |
|---|---|---|---|---|
| 30 | CH₃CH—CH₂$\overset{*}{C}$H <br>      \|     \| <br>     CH₃  Cl | (phenyl-pyrimidine)—C₈H₁₇ | 80–82 | $[\alpha]_D^{21}$: −63.4° |
| 31 | C₈H₁₇O—(phenyl)—C(=O)O— | $\overset{*}{C}$H—CH₂—CH₃ <br>  \| <br>  CH₃ | oil | $[\alpha]_D^{21}$: −34.4° |
| 32 | C₁₀H₂₁—O—(phenyl)— | (phenyl)—O—$\overset{CH_3}{\underset{*}{C}H}$—COOC₂H₅ | oil | $[\alpha]^{21}$: −54.2° |
| 33 | " | (phenyl-pyrimidine)—OC₈H₁₇ | oil | $[\alpha]_D^{21}$: −20.2° |
| 34 | C₅H₁₁ | " | 69–72 | $[\alpha]_D^{21}$: −52.0° |
| 35 | C₁₀H₂₁—O—(phenyl)— | (phenyl-pyrimidine)—S—C₈H₁₇ | 79–80 | $[\alpha]_D^{21}$: −19.8° |
| 36 | C₅H₁₁ | " | oil | $[\alpha]_D^{21}$: −50.8° |
| 37 | H₅C₂—$\overset{*}{C}$H—$\overset{*}{C}$H <br>     \|    \| <br>    CH₃ Cl | (phenyl-pyrimidine)—C₈H₁₇ | 81–82 | $[\alpha]_D^{21}$: −63.4° |
| 38 | H₂₁C₁₀O—(phenyl)—C(=O)O— | $\overset{*}{C}$H—C₂H₅ <br>  \| <br>  CH₃ | oil | $[\alpha]_D^{21}$: −31.8° |
| 39 | H₁₇C₈O—(phenyl)—C(=O)O— | $\overset{*}{C}$HCO₂C₂H₅ <br>  \| <br>  CH₃ | −10 | $[\alpha]_D^{21}$: −53.0° |
| 40 | " | CH₂—$\overset{*}{C}$H—CH₃ <br>      \| <br>     Cl | 16[a] | $[\alpha]_D^{21}$: −22.7° |
| 41 | H₁₇C₈—(biphenyl)— | CH₃ | 78–79 | $[\alpha]_D^{21}$: −34.3° |
| 42 | " | C₈H₁₇ | 28–29 | $[\alpha]_D^{21}$ −27.3 |
| 43 | H₁₇C₈—(biphenyl)— | C₈H₁₇ | 60–61 | $[\alpha]_D^{21}$: −29.1° |

TABLE I-continued

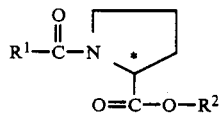

| Example No. | R¹ | R² | C [°C.] | Rotation [degree] (C = 1, CH₂Cl₂) |
|---|---|---|---|---|
| 44 | H₁₇C₈—[pyrimidine-phenyl] | C₄H₉ | oil | $[\alpha]_D^{21}$: −28.3° |

(a) clear point

USE EXAMPLES

In order to test the activity of the compounds described above as dopes in liquid-crystal systems, they are mixed in concentrations of in each case 10 mol % (or in individual cases of 5 and 17.5 mol %) with the racemate of the compound

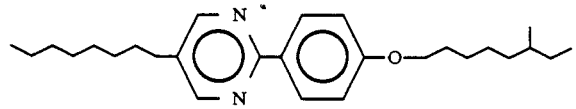

4-(5-octylpyrimidin-2-yl)-1-(6-methyloct-1-oxy)benzene (Table II) or the compound

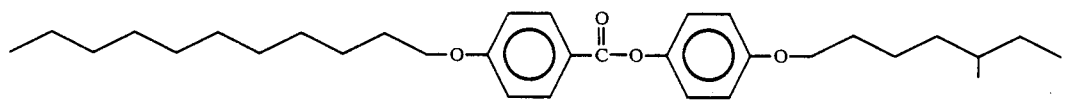

4-(4-undecyloxyphenyl-1-carbonyloxy)-1-(5-methylheptyloxy)-benzene (Table III), and in each case the values for spontaneous polarization ($P_s$ in nC.cm⁻²), for the switching time τ (in μs) and for the optical tilt angle θ of the $S_c$ phase (in °) of the mixture are determined. The $P_s$ values are measured by the method of Sawyer et al. (Phys. Rev. 35, 269 to 273, 1930), a special measuring cell [Skarp et al. in Ferroelectric Letters Vol. 06, 67 (1986)] being used in which the τ and θ values are also determined. At a cell path length of about 2 μm, a uniform planar orientation of the liquid crystals in the $S_C$ phase is achieved by applying a shear force [SSFLC technology, Clark et al., Appl. Phys. Lett. 36, 899 (1980)]. In order to determine τ and θ, the measurement cell is clamped on the rotary stage of a polarization microscope between a crossed analyzer and polarizer. By rotating the measurement cell from maximum to minimum light transmission, the optical tilt angle or switching angle, 2θ, is determined. The switching time, τ, is determined with the aid of a photodiode by measuring the time for the light signal to increase from a signal level of 10 to 90%. Tables II and III sumarize the results for the mixtures. In addition to the values for $P_s$, τ and 2θ, the $S_c$* range for the particular mixture is given; the values in parentheses here give the supercoolable lower temperature limit of the $S_c$* range.

Table II

| Example No. | Proportion of the chiral comp. in mol % | $S_c$* range of the mixture (°C.) | in each case at 25° C. | | |
|---|---|---|---|---|---|
| | | | Ps (nC/cm²) | τ (μs) | 2θ (degree) |
| 2 | 10 | 13.5 [5]–45 | 12 | 55 | 36 |
| 16 | 10 | 14.5 [2]–43 | 6.5 | 45 | 40 |
| 17 | 10 | 13.5 [3]–43 | 10.5 | 70 | 40 |
| 18 | 10 | 13.5 [5]–45 | 11.5 | 50 | 33 |
| 19 | 10 | 15 [10]–42 | 7.5 | 45 | 40 |
| 20 | 10 | 15 [5]–43 | 4.5 | 80 | 35 |
| 21 | 10 | 13 [10]–48 | 6 | 100 | 39 |
| 22 | 10 | 13 [4]–48 | 13.1 | 40 | 42 |
| 30 | 5 | 20–45 | 19.5 | 60 | 34 |

Table III

| Example No. | Proportion of the chiral comp. in mol % | $S_c$* range of the mixture (°C.) | in each case at 40° C. | | |
|---|---|---|---|---|---|
| | | | Ps (nC/cm²) | τ (μs) | 2θ (degree) |
| 1 | 10 | 32–50 | 5 | 50 | 32 |
| 3 | 10 | 21–59 | 31 | 35 | 62 |
| 4 | 10 | 30 [25]–50 | 3.4 | 150 | 50 |
| 5 | 10 | 23.2–50 | 4 | 190 | 47 |
| 11 | 10 | 25–59 | 20 | 43 | 53 |
| 13 | 10 | 20–59 | 31 | 50 | 51 |
| 15 | 10 | 18–58 | 25 | 40 | 54 |
| 15 | 17.5 | 20–53 | 80 | 195 | 46 |
| 26 | 10 | 37 [28]–58 | 20 | 30 | 57 |
| 27 | 10 | 38 [27]–61 | 30 | 40 | 54 |
| 31 | 5 | 30–65 | 16 | 52 | 59 |
| 31 | 10 | 20–60 | 38 | 29 | 53 |
| 31 | 17.5 | 17.5–54 | 48 | 31 | 51 |
| 37 | 5 | 20–45 | 20 | 60 | 34 |
| 39 | 10 | 25–58 | 14 | 40 | 55 |
| 40 | 10 | 18–60 | 23 | 30 | 54 |
| 42 | 10 | 18–54 | 3 | 50 | 44 |
| 44 | 10 | 20–60 | 19 | 45 | 44 |

We claim:

1. A liquid-crystal mixture containing at least two components, wherein at least one component is an optically active ester of 1-acylproline of the formula (I)

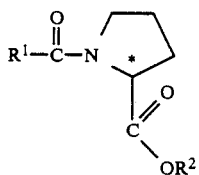

(I)

in which one of $R^1$ or $R^2$ is a mesogenic radical of the formulas (II), (III) or (IV)

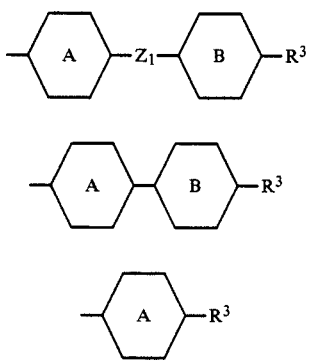

where the indices and components have the following meanings:

$Z_1$=COO, OOC, (CH$_2$)$_2$, OCH$_2$, CH$_2$O, or CH$_2$,

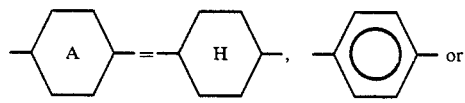

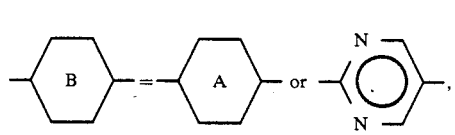

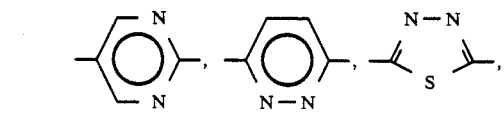

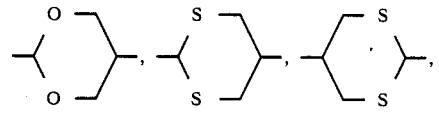

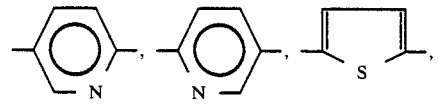

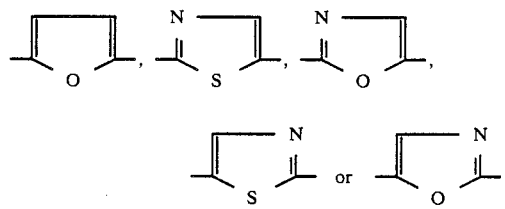

$R^3=C_rH_{2r+1}$, $OC_rH_{2r+1}$, $SC_rH_{2r+1}$,

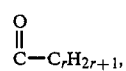

OOC—$C_rH_{2r+1}$, COO$C_rH_{2r+1}$ or NHC$_4$H$_{2r+1}$, where r is an integer from 1 to 12, and in which the other radical $R^1$ or $R^2$ is: a straight-chain or branched alkyl group which has 1–12 carbon atoms, which is unsubstituted or substituted by F, Cl, Br or CN, in which one or two non-neighboring —CH$_2$-groups may be replaced by —O—, —S—, —CO—, —OCO—, —COO—, —OCS—, —COS—, —CH═CH$_{13}$, and or

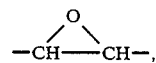

and which can contain a terminal group —CH═CH$_2$ or

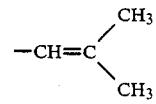

or which is cyclohexyl or phenyl, or 4-alkylcyclohexyl or 4-alkylphenyl or 4-alkoxyphenyl having 1–6 carbon atoms in the alkyl.

2. A liquid-crystal mixture as claimed in claim 1, wherein at least one of the radicals $R^1$ and $R^2$ in formula (I) is a mesogenic radical selected from the group consisting of

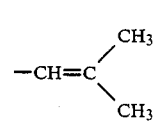

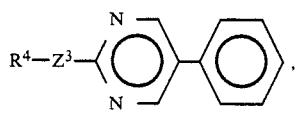

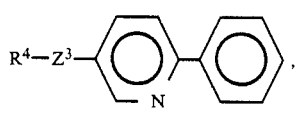

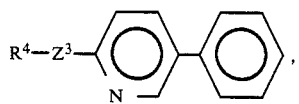

-continued

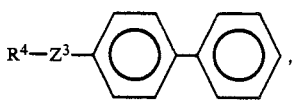,

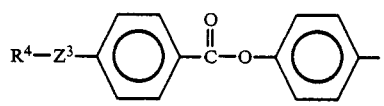

where $Z_3$ is a chemical bond, an oxygen atom, a sulfur or a carboxyl group, and $R^4$ is a straight-chain or branched, saturated alkyl group having 6-12 carbon atoms.

3. A liquid-crystal mixture as claimed in claim 2, wherein the nonmesogenic radical is a cyclohexyl group, a phenyl, alkylphenyl or alkoxyphenyl group, a straight-chain or branched alkyl group having 1-10 carbon atoms, an unsaturated alkyl group having 2-10 carbon atoms or an alkyl group in which one —$CH_2$- group is replaced by an optically active moiety selected from the group consisting of

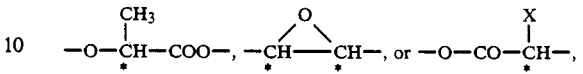

where X=F, Cl, Br or CN.

4. A display element comprising a liquid-crystal mixture containing at least one optically active ester of 1-acylproline as claimed in claim 1.

* * * * *